United States Patent
Hes et al.

(10) Patent No.: US 8,636,785 B2
(45) Date of Patent: Jan. 28, 2014

(54) BONE SCREW

(75) Inventors: Robert Hes, Antwerp (BE); Bart Conix, Zoersel (BE); Christopher Gowland, Pontefract (GB)

(73) Assignee: Globus Medical, Inc., Audubon, PA (US)

( * ) Notice: Subject to any disclaimer, the term of this patent is extended or adjusted under 35 U.S.C. 154(b) by 855 days.

(21) Appl. No.: 10/583,422

(22) PCT Filed: Dec. 16, 2004

(86) PCT No.: PCT/GB2004/005280
§ 371 (c)(1),
(2), (4) Date: Apr. 16, 2007

(87) PCT Pub. No.: WO2005/058175
PCT Pub. Date: Jun. 30, 2005

(65) Prior Publication Data
US 2007/0282341 A1    Dec. 6, 2007

(30) Foreign Application Priority Data

Dec. 19, 2003 (GB) .................................. 0329596.1
Mar. 25, 2004 (GB) .................................. 0406825.0

(51) Int. Cl.
*A61B 17/86* (2006.01)
(52) U.S. Cl.
USPC .......................................... 606/315; 606/317

(58) Field of Classification Search
USPC .................................................. 606/300–321
See application file for complete search history.

(56) References Cited

U.S. PATENT DOCUMENTS

| | | | |
|---|---|---|---|
| 5,180,382 A * | 1/1993 | Frigg et al. ...................... | 606/65 |
| 5,735,653 A | 1/1993 | Frigg | |
| 5,259,398 A * | 11/1993 | Vrespa .......................... | 128/898 |
| 5,593,410 A * | 1/1997 | Vrespa .......................... | 606/312 |
| 5,743,914 A | 4/1998 | Skiba | |
| 5,779,704 A | 7/1998 | Kim | |
| 6,030,162 A | 2/2000 | Huebner | |
| 6,129,730 A * | 10/2000 | Bono et al. .................... | 606/291 |
| 6,355,043 B1 * | 3/2002 | Adam ............................. | 606/62 |
| 7,811,312 B2 * | 10/2010 | Stevens et al. ................ | 606/280 |
| 2006/0282074 A1 | 12/2006 | Renaud | |
| 2007/0282341 A1 | 12/2007 | Hes et al. | |
| 2008/0208259 A1 | 8/2008 | Gilbert | |
| 2008/0288002 A1 | 11/2008 | Crall | |

* cited by examiner

*Primary Examiner* — Matthew Lawson

(57) ABSTRACT

A bone screw (10) having a lead portion (12) and a tail portion (14), each comprising a root and a thread (22, 24) (having a thread lead) formed on the root. The thread on each of the lead and tail portions has an approximately constant diameter along a significant portion of its length. The diameter of the thread on the tail portion is greater than that of the thread on the lead portion, and in which the thread lead of the thread on the lead portion is equal to the thread lead of the thread on the tail portion. The screw can be used to achieve fixation to a vertebra with an anterior approach.

10 Claims, 2 Drawing Sheets

BONE SCREW

This invention relates to a bone screw. The bone screw can be used for example for screw fixation to a vertebra.

Bone screws can be used to fasten components to bone tissue. For example, bone screws can be used to fasten implant components to a bone. Examples of implant components include fracture plates which can be fastened across a fracture to hold fractured parts of a bone in alignment during healing. Bone screws can be used to fasten instruments to bone during surgery. Examples of instruments which might require such fastening include alignment rods and resection blocks.

A bone screw can be used to fasten a component to a vertebra, for example in the treatment of a defect in a patient's spine such as a fracture within a vertebra, or a defective (for example degenerative) inter-vertebral body (disc). For example, a bone screw can be used to fasten anchor blocks to a vertebra. A bar or plate can be connected to the spine at a number of vertebrae using such anchor blocks, to immobilise (for example by fusing) a segment of the spine.

Screws used for fixation to a vertebra are commonly referred to pedicle screws. An example of a pedicle screw is disclosed in WO-90/02526. Pedicle screws are conventionally inserted using a posterior approach, in which the screw extends through the pedicle into the vertebral body.

Bone in the vertebral body comprises cancellous bone tissue, characterised by voids and a low density. Bone in the pedicles comprises cortical bone tissue, which has a higher density than cancellous bone tissue. Cortical bone tissue is stronger than cancellous bone tissue and is better able to provide a secure connection for screw fixation. However, the width of the bone screw is restricted by the narrow transverse dimension of the pedicle. It can therefore mean that the contribution of the cancerous bone tissue to the screw fixation is significantly compromised because the structure of the cancellous bone requires that the thread has a large diameter in order for the fixation to it to be secure.

The present invention provides a bone screw which can be used for fixation to a bone whose structure or dimensions differ from one region to another, which has lead and tail portions, each having an approximately constant diameter over a significant portion of its length, in which the diameter of the thread on the tail portion is greater than that of the thread on the lead portion, and in which the thread lead of the thread on the lead portion is equal to the thread lead of the thread on the tail portion.

Accordingly, in one aspect, the invention provides a bone screw having a lead portion and a tail portion, each comprising a root and a thread (having a thread lead) formed on the root, the thread on each of the lead and tail portions having an approximately constant diameter along a significant portion of its length, in which the diameter of the thread on the tail portion is greater than that of the thread on the lead portion, and in which the thread lead of the thread on the lead portion is equal to the thread lead of the thread on the tail portion.

The bone screw of the invention has the advantage that it can be used to form a secure fixation to a bone which has regions with different characteristics such as dimensions, bone density, in which the lead portion of the screw is received in a first region of the bone and the tail portion of the screw is received in a second region. For example, the bone in the first region might comprise cortical tissue and the bone in the second region might comprise cancellous tissue. The transverse dimension of the bone in the first region might be smaller than that in the second region.

The bone screw of the invention finds particular application in screw fixation to a vertebra, in which the screw is inserted into the vertebra anteriorly, via the vertebral body into a pedicle.

The lead and tail portions of the bone screw should be connected to one another so that it is not possible for one of them to be rotated relative to the other, preferably in both rotational directions. This can be achieved by forming the bone screw as a single body, for example by a moulding (casting) process, or by machining the screw from a single block (especially a single block of a metal). If the lead and tail portions of the screw are formed as separate parts, they should generally be capable of being fastened to one another so that they are incapable of relative rotation in at least one, preferably each direction. This allows the bone screw to be driven into a bone by the application of rotational forces from the tail end.

In another aspect, the invention provides a method of screw fixation to a vertebra, which comprises exposing an anterior surface of the vertebra to receive a screw, and inserting a bone screw into the vertebra, via the vertebral body into a pedicle. The screw that is used in the method can be a bone screw according to the invention.

Significant advantages arise from insertion of a bone screw into a vertebra using an anterior approach. Exposure of bone tissue anteriorly involves less resection of muscle and other tissue compared with a posterior approach. This can give rise to advantages of reduced blood loss, reduced patient trauma, and reduced recovery time.

Furthermore, insertion of a bone screw into a pedicle through the cancellous tissue of the vertebral body allows the screw to be constructed with threads whose features are optimised for fixation to the bone tissues in the two regions of the bone. In particular, the diameter of the tail portion of the screw can be greater than the diameter of the lead portion: a large diameter in the tail portion can enhance the security of the fixation in the cancellous tissue.

Preferably, the thread on the lead portion of the screw is a multi-start thread. This has the advantage of providing a thread on the lead portion which has a smaller pitch than would be the case if the thread is a single-start thread. This can enhance the security of the fixation in cortical bone tissue.

Preferably, the number of starts of the thread on the lead portion is equal to the ratio of the thread pitch of the thread on the tail portion to the thread pitch of the thread on the lead portion. For example, the thread on the lead portion of the screw can be a double-start thread with the thread on the tail portion of the screw being a single-start thread; preferably, the thread pitch of the thread on the tail portion is then equal to twice the thread pitch of the thread on the lead portion.

The thread pitch is the distance along the axis of the screw between adjacent thread peaks. The thread lead is the distance that is travelled along the axis of the screw in one complete 360° revolution of the screw. When the thread on the lead portion of the screw is a multi-start thread, it is preferred that the number of starts of the thread is equal to the ratio of the thread lead to the thread pitch.

Preferably, the ratio of the diameter of the thread on the tail portion to that of the diameter of the thread on the lead portion is at least about 1.2, more preferably at least about 1.5. When the bone screw is intended for use in a vertebra, the relative sizes of the lead and tail portions of the screw can be selected to ensure that the diameter of the lead portion is not greater than the transverse dimension of the pedicle, while also providing sufficiently large diameter in the tail portion to provide secure fixation in the cancellous tissue. Preferably, the ratio of the diameter of the thread on the tail portion to the diameter of the thread on the lead portion is not more than about 2.3, preferably not more than about 2.0.

Generally, the diameter of the root of the tail portion is greater than the diameter of the root of the lead portion. The ranges for the ratio of the diameter of the thread on the tail portion to the diameter of the thread on the lead portion can also apply to the ratio of the diameter of the root of the tail portion to the diameter of the root of the lead portion.

Preferably, the diameter of the lead portion of the bone screw is at least about 3 mm, more preferably at least about 4.5 mm, for example at least about 6 mm. Preferably, the diameter of the lead portion of the screw is not more than about 15 mm, more preferably not more than about 13 mm, for example not more than about 11 mm.

Preferably the diameter of the root of the lead portion is at least about 2.5 mm, more preferably at least about 3.5 mm, for example at least about 4 mm. Preferably, the diameter of the root of the lead portion is not more than about 7 mm, more preferably not more than about 6 mm, for example not more than about 5 mm.

Preferably the diameter of the root of the tail portion is at least about 3 mm, more preferably at least about 4 mm, for example at least about 5 mm. Preferably, the diameter of the root of the tail portion is not more than about 10 mm, more preferably not more than about 8 mm, for example not more than about 7 mm.

Preferably, the ratio of the diameter of the root of the tail portion to the diameter of the root of the lead portion is at least about 1.2, more preferably at least about 1.4. Preferably, the ratio of the diameter of the root of the tail portion to the diameter of the root of the lead portion is not more than about 2.3, more preferably not more than about 2.0.

Preferably, the value of the thread aspect ratio, defined by the expression;

$$\text{Thread aspect ratio} = \frac{(\text{Overall diameter}) - (\text{Root diameter})}{2 \times (\text{Root diameter})}$$

in respect of the thread on the tail portion is greater than that in respect of the thread on the lead portion. It has been found that a higher thread aspect ratio for the thread on the tail portion can help to make a secure screw fixation to cancellous bone. For example, the ratio of the thread aspect ratio of the thread on the tail portion to the thread aspect ratio of the thread on the lead portion might be at least about 1.2, preferably at least about 1.35. Preferably, the ratio of the thread aspect ratio of the thread on the tail portion to the thread aspect ratio of the thread on the lead portion is not more than about 2.2, more preferably not more than about 2.0.

For example, the thread aspect ratio in the lead portion might be at least about 0.15, preferably at least about 0.2. The thread aspect ratio in the lead portion might be not more than about 0.4, preferably not more than about 0.3, especially not more than 0.25. The thread portion of the tail portion might be at least about 0.25, preferably at least about 0.3. The thread aspect ratio in the tail portion might be not more than about 0.5, preferably not more than about 0.4, especially not more than 0.35.

Preferably, the bone screw has a bore extending through it along its length. This can facilitate use of a guidewire to locate and to orientate the bone screw. The bone screw of the invention can be supplied as a part of a kit, which also includes a guidewire which is a close fit in the bore in the bone screw.

Materials for the bone screw should be inert towards body fluid with which the screw will come into contact when it is in use. It should also be capable of withstanding the stresses to which it will be subjected during fixation and once fixed to the bone. Suitable materials include certain stainless steel alloys, and titanium and certain titanium based alloys. Materials which can be used in the manufacture of bone screws are known.

Preferably, the thread at the end of the lead portion of the screw is self-starting. For example, the diameter of the thread towards the end of the lead portion can be reduced towards the end of the screw, relative to the diameter of the thread on the lead portion where it is approximately constant.

Preferably, the screw has a transition portion between the lead and tail portions. For example; the diameter of the screw can increase gradually between the lead and tail portions over the transition portion. The bone screw can comprise a root with a thread formed on it in the transition portion; preferably, the thread in the transition portion is a continuation of the thread on the tail portion, in which the diameter of the thread in the transition portion is reduced towards the lead portion.

Preferably, the thread on the tail portion of the screw is a continuation of the thread on the lead portion. When the thread on the lead portion of the screw is a multi-start thread, the thread on the tail portion of the screw is preferably a continuation of one of the threads on the lead portion.

The bone screw will generally be provided with formations at its tail end for engaging a tool by which torque can be applied to the screw to drive it into the bone. Suitable formations include recesses shaped as, for example, slots, crosses, stars, polygons (especially hexagons), and multiple lobes (especially hexlobes).

Embodiments of the invention will now be described by way of example with reference to the accompanying drawings, in which.

Figure 1:
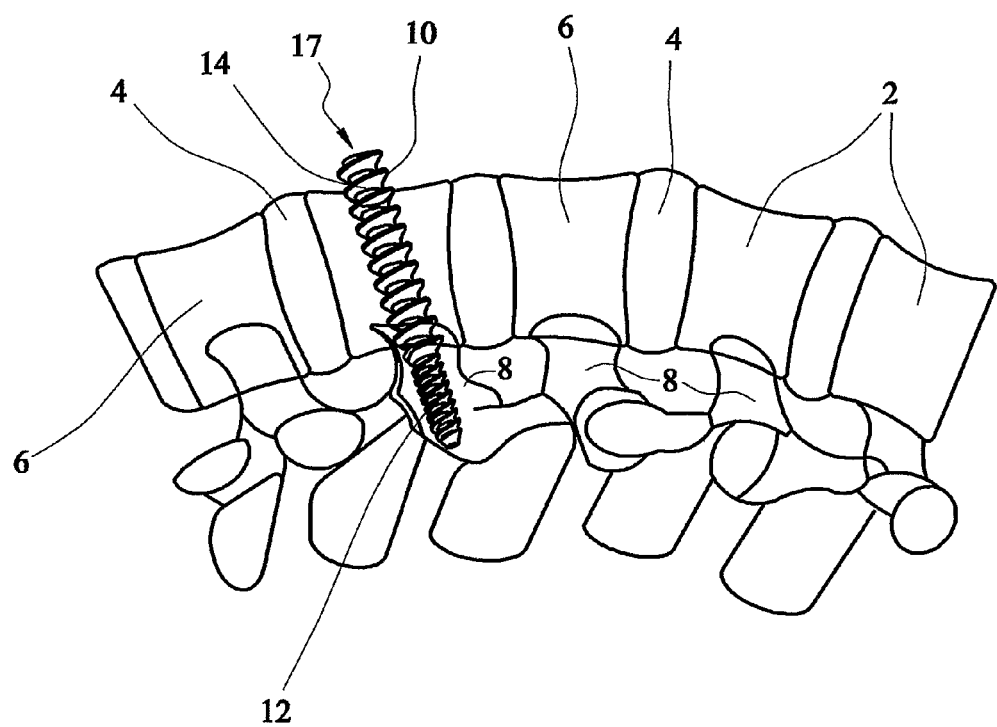
FIG. 1 is a schematic side view of a portion of a spine, having a vertebra in which a bone screw according to the invention has been implanted.

Referring to the drawings, FIG. 1 shows a portion of a spine which comprises a plurality of vertebrae 2 separated by disks 4. Each of the vertebrae 2 comprises a vertebral body 6 and two posteriorly directed pedicles (of which one 8 is visible on each of the vertebrae).

Conventionally, a bone screw is inserted into a vertebra using a posterior approach so that the screw passes through the cortical bone of a pedicle into the cancellous bone of the vertebral body.

According to the invention, a bone screw 10 is implanted into a vertebra using an anterior approach, so that the screw passes through the cancerous bone of the vertebral body 6 into the cortical bone of the pedicle 8.

Figure 2:
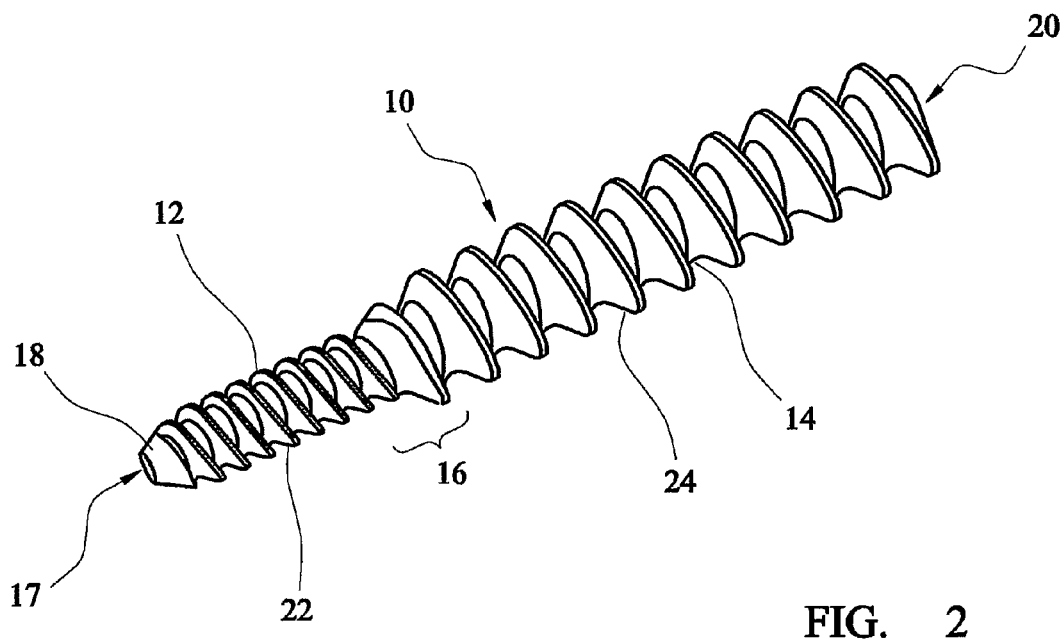
FIG. 2 is a side view of a bone screw of the kind which is shown in FIG. 1 implanted in a vertebra.

FIG. 2 shows a bone screw 10 which is configured for implantation into a vertebra using an anterior approach. The screw has a lead portion 12 and a tail portion 14. and an intermediate transition portion 16. Each of them comprises a root which has a helical thread formed on it. The screw has a bore 17 extending through it.

The thread on each of the lead and tail portions has a constant diameter over almost the entire length of the respective portion. The tip 18 of the bone screw is tapered towards a point. The opposite end of the bone screw has a hexagonal socket 20 formed in it which can receive the end of a hexagonal driver tool.

Figure 3:
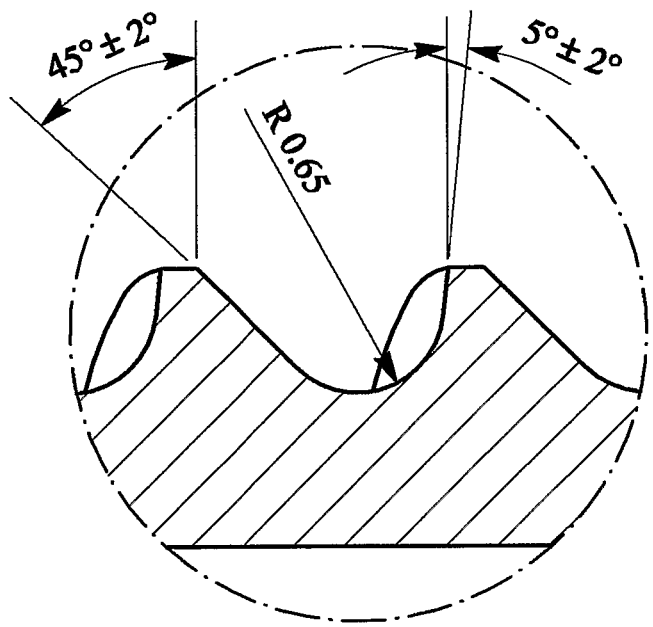
FIGS. 3 and 4 are enlarged side views showing details of the threads on the bone screw shown in FIG. 2, in the lead and tail portions.

The thread 22 on the lead portion is a double-start thread, in which two threads are arranged around the root, equally spaced around the axis of the screw. The thread is optimised in terms of the aspect ratio for fixation in cortical bone tissue. Because the thread on the lead portion is a double-start thread, the thread pitch on the lead portion is equal to half the thread lead. Details of the thread 22 are shown in FIG. 3.

Figure 4:
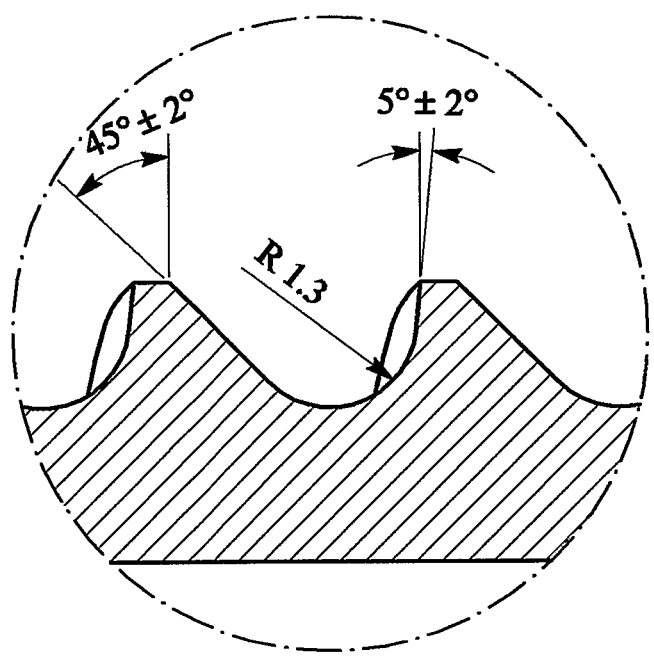

The thread 24 on the tail portion is a single-start thread, in which the thread pitch and the thread lead are equal to the thread lead on the lead portion. The thread is optimised in terms of the aspect ratio for fixation in cancellous bone tissue. The thread on the tail portion is continuous with one of the threads on the lead portion, through the transition portion of the screw in which the root and the thread taper. Details of the thread 24 are shown in FIG. 4.

Dimensions (in millimeters) of a preferred embodiment of screw, which can be suitable for use as a pedicle screw, are as follows:

| | | |
|---|---|---|
| Overall | Length | 70.0 |
| | Bore diameter | 2.0 |
| Lead portion | Length | 20.0 |
| | Thread pitch | 2.25 |
| | Thread lead | 4.5 |
| | Root diameter | 4.5 |
| | Overall diameter | 6.5 |
| | Thread aspect ratio | 0.22 |
| Tail portion | Length | 46.0 |
| | Thread pitch | 4.5 |
| | Thread lead | 4.5 |
| | Root diameter | 6.5 |
| | Overall diameter | 10.5 |
| | Thread aspect ratio | 0.31 |

The invention claimed is:

1. A bone screw having a lead portion and a tail portion, and an intermediate transition portion, each of the lead portion and the tail portion comprising a root and a helical thread formed on the root, the thread on the lead portion having a diameter and the thread of the tail portion having a diameter wherein the diameter of the thread on the tail portion is greater than that of the thread on the lead portion, wherein the thread on the lead portion extends to a distal end of the screw, wherein the lead portion includes a first section in which the thread of the lead portion is of a constant diameter and a second section closer to the distal end of the screw in which the thread of the lead portion is of a reduced diameter relative to the thread of the lead portion that is of a constant diameter,
wherein the intermediate transition portion is configured between the threads of the lead portion and the tail portion,
wherein the tail portion is provided with a socket end, wherein the socket end of the tail portion is adapted to be flush with the surface of the bone or under the surface of the bone after the bone screw is fully inserted,
wherein the thread on the lead portion of the screw is a double-start thread and the thread on the tail portion of the screw is a single-start thread, and in which the thread pitch of the thread on the tail portion is greater than the thread pitch of the thread on the lead portion, and wherein the single-start thread on the tail portion is a continuation of one of the threads of the double-start thread on the lead portion,
wherein the thread aspect ratio of the thread on the tail portion is greater than the thread aspect ratio of the thread on the lead portion,
wherein the lead portion and the tail portion are formed from a single block of metal,
wherein a bore extends through the bone screw throughout its entire length.

2. A bone screw as claimed in claim 1, in which the thread on the lead portion of the screw is a multi-start thread.

3. A bone screw as claimed in claim 2, in which the number of starts of the thread on the lead portion is equal to the ratio of the thread pitch of the thread on the tail portion to the thread pitch of the thread on the lead portion.

4. A bone screw as claimed in claim 1, wherein the lead portion and tail portion of the bone screw comprises a stainless steel alloy.

5. A bone screw as claimed in claim 1, wherein the lead portion and tail portion of the bone screw comprises titanium.

6. A bone screw as claimed in claim 1, in which the diameter of the root of the tail portion is greater than the diameter of the root of the lead portion.

7. A bone screw as claimed in claim 1, wherein the lead portion and the tail portion of the bone screw comprises a titanium alloy.

8. A bone screw as claimed in claim 1, wherein the bone screw has a distal tip that is tapered.

9. A bone screw as claimed in claim 1, wherein the socket end of the bone screw comprises a hexagonal socket.

10. A bone screw having a lead portion and a tail portion, and an intermediate transition portion, each of the lead portion and the tail portion comprising a root and a helical thread formed on the root, the thread of the lead portion having a diameter and the thread of the tail portion having a diameter wherein the diameter of the thread on the tail portion is greater than that of the thread on the lead portion, wherein the intermediate transition portion is configured between the threads of the lead portion and the tail portion, and wherein a root diameter of the lead portion is less than a root diameter of the tail portion and wherein the thread on the lead portion of the screw is a double-start thread and the thread on the tail portion of the screw is a single-start thread, and wherein the thread pitch of the thread on the tail portion is greater than the thread pitch of the thread on the lead portion, wherein the single-start thread on the tail portion is a continuation of one of the threads of the double-start thread on the lead portion, and wherein the thread aspect ratio of the thread on the tail portion is greater than the thread aspect ratio of the thread on the lead portion, wherein the lead portion and the tail portion are formed from a single block of metal, wherein the thread on the lead portion extends to a distal end of the screw, wherein the lead portion includes a first section in which the thread of the lead portion is of a constant diameter, wherein a bore extends through the bone screw throughout its entire length.

* * * * *